(12) United States Patent
Anderson et al.

(10) Patent No.: US 8,232,332 B2
(45) Date of Patent: Jul. 31, 2012

(54) CURED HYDROPHILIC COMPOSITIONS

(75) Inventors: Kelly S. Anderson, Houlton, WI (US); Kevin M. Lewandowski, Inver Grove Heights, MN (US); David J. Plaut, Minneapolis, MN (US); Wendy L. Thompson, Roseville, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/161,672

(22) Filed: Jun. 16, 2011

(65) Prior Publication Data

US 2011/0245077 A1 Oct. 6, 2011

Related U.S. Application Data

(62) Division of application No. 11/419,779, filed on May 23, 2006, now Pat. No. 7,981,949.

(51) Int. Cl.
*C03C 25/26* (2006.01)

(52) U.S. Cl. ........ 523/203; 523/200; 523/202; 523/212; 523/213; 524/547; 524/555; 524/558; 524/588; 524/599; 524/606; 524/609; 524/612

(58) Field of Classification Search ................... 502/402; 523/200, 202, 203, 212, 213; 524/547, 555, 524/558, 588, 599, 606, 609, 612; 977/773
See application file for complete search history.

(56) References Cited

U.S. PATENT DOCUMENTS

| | | |
|---|---|---|
| 2,801,185 A | 7/1957 | Iler |
| RE24,906 E | 12/1960 | Ulrich |
| 3,121,021 A | 2/1964 | Copeland |
| 3,389,827 A | 6/1968 | Abere et al. |
| 4,112,213 A | 9/1978 | Waldman |
| 4,373,519 A | 2/1983 | Errede et al. |
| 4,499,896 A | 2/1985 | Heinecke |
| 4,522,958 A | 6/1985 | Das et al. |
| 4,598,004 A | 7/1986 | Heinecke |
| 4,849,458 A | 7/1989 | Reed et al. |
| 5,126,394 A | 6/1992 | Revis et al. |
| 5,204,219 A | 4/1993 | Van Ooij et al. |
| 5,464,900 A | 11/1995 | Stofko et al. |
| 5,531,855 A | 7/1996 | Heinecke et al. |
| 5,614,310 A | 3/1997 | Delgado et al. |
| 5,639,546 A | 6/1997 | Bilkadi |
| 5,648,407 A | 7/1997 | Goetz et al. |
| 5,653,699 A | 8/1997 | Reed et al. |
| 5,733,570 A | 3/1998 | Chen et al. |
| 5,738,642 A | 4/1998 | Heinecke et al. |
| 5,849,325 A | 12/1998 | Heinecke et al. |
| 6,171,985 B1 | 1/2001 | Joseph et al. |
| 6,198,016 B1 | 3/2001 | Lucast et al. |
| 6,391,952 B1 | 5/2002 | Bett et al. |
| 6,467,897 B1 | 10/2002 | Wu et al. |
| 6,468,451 B1 | 10/2002 | Perez et al. |
| 6,566,575 B1 | 5/2003 | Stickels et al. |
| 6,960,275 B2 | 11/2005 | Vesley et al. |
| 7,005,143 B2 | 2/2006 | Abuelyaman et al. |
| 2001/0051178 A1 | 12/2001 | Blatchford et al. |
| 2002/0022672 A1 | 2/2002 | Thunhorst et al. |
| 2003/0060533 A1 | 3/2003 | Ohtsuki et al. |
| 2004/0235997 A1 | 11/2004 | Meisenburg et al. |
| 2005/0113489 A1 | 5/2005 | Baran, Jr. et al. |
| 2005/0151119 A1 | 7/2005 | Jones et al. |
| 2005/0194559 A1 | 9/2005 | Lewandowski et al. |
| 2005/0200278 A1 | 9/2005 | Jones et al. |
| 2005/0256223 A1 | 11/2005 | Kolb et al. |
| 2006/0034935 A1 | 2/2006 | Pronovost et al. |
| 2006/0039982 A1 | 2/2006 | Abuelyaman et al. |
| 2006/0229377 A1 | 10/2006 | Bublewitz et al. |

FOREIGN PATENT DOCUMENTS

| | | |
|---|---|---|
| EP | 0 372 756 | 6/1990 |
| WO | WO 99/13865 | 3/1999 |
| WO | WO 99/13866 | 3/1999 |
| WO | WO 00/42958 | 7/2000 |
| WO | WO 01/60296 | 8/2001 |
| WO | WO 03/022935 | 3/2003 |
| WO | WO 03/086493 | 10/2003 |
| WO | WO 2005/051846 | 6/2005 |

OTHER PUBLICATIONS

Tanahashi, et al., "Adsorption of Poly (N-isopropylacrylamide) on Silica Surfaces," Macromolecules, vol. 27, pp. 606-607, 1994.

*Primary Examiner* — David W Wu
*Assistant Examiner* — Marie Reddick
(74) *Attorney, Agent, or Firm* — Kent S. Kokko

(57) ABSTRACT

A curable composition is described, including a gel material derived from the curable composition, and medical articles including such material, wherein the transparent gel material includes a polymerized monofunctional poly(alkylene oxide) macromonomer component and a surface modified nanoparticle component.

14 Claims, No Drawings

CURED HYDROPHILIC COMPOSITIONS

CROSS REFERENCE TO RELATED APPLICATIONS

This application is a divisional of U.S. application Ser. No. 11/419,779, filed May 23, 2006, now U.S. 7,981,949, the disclosure of which is incorporated by reference in its entirety herein.

BACKGROUND

The present invention is directed to curable hydrophilic compositions, gel materials comprising the cured hydrophilic compositions, and medical articles incorporating such materials, particularly medical articles useful as wound dressings. More particularly this invention is directed to curable hydrophilic compositions prepared from a monofunctional poly (alkylene oxide) macromonomer and surface modified nanoparticles.

Historically, exudate from a wound has been treated by absorbing it using a dressing containing an absorbent material. Typical such dressings contain a padded absorbent material attached to an adhesive tape backing The padded absorbent material is applied to the wound to absorb the wound exudate. A difficulty with this type of dressing is that the scab typically forms in and as part of the pad as the wound heals. Thus, when the dressing is removed, the scab is removed. This problem has been addressed by providing a porous film between the absorbent material and the wound to reduce the likelihood that a scab formed will become attached to the absorbent material.

More recently the use of so-called "occlusive" dressings for pressure sores and ulcers has gained increasing acceptance. A number of wound dressings of this kind are commercially available. Most of these products are formed from several layers, including at least an inner skin-contacting layer and an outer backing layer. The dressing is applied as a cover for the sore or ulcer in a size providing a margin around the wound area that adhesively seals to the skin. The inner layer contains water-absorptive materials, so that fluid from the wound is absorbed into the layer, making it possible to keep the dressing in place for at least several days. Such occlusive dressings tend to promote healing by maintaining the wound under moist conditions without forming a crust, and serving as a barrier against bacterial infection. Such dressings for "moist wound healing" are particularly useful for dermal burns, traumatic skin deficiencies, incised wounds, and the like.

A wound care product in current use utilizes a hydrocolloid absorbent. Such a material typically has poor transparency so the treatment state cannot be observed from the outside. Also, such a material can partially lose its integrity after absorbing wound fluid. Flexibility of hydrocolloid dressings can be poor, which makes it difficult to apply the dressing to a bend portion of a body, such as a joint, etc. The portion of the absorbent in contact with the wound is converted to a gel-like material, and, when the dressing is removed, a portion of this absorbent material can be left in the wound, and must be removed to permit examination and/or before applying another dressing.

There are known hydrophilic gel materials useful in medical applications such as wound dressings, however, many of them do not have the appropriate balance of absorption and cohesive strength often needed. Thus, additional such materials are needed. Furthermore, it be desirable to provide an occlusive material that is also transparent and flexible for use in a medical article such as a wound dressing or wound packing material.

SUMMARY OF THE INVENTION

This invention provides curable hydrophilic compositions, polymeric gel materials comprising the cured compositions, and medical articles comprising the gel materials for use therein, which are preferably absorbent, and more preferably absorbent and transparent.

The curable composition comprises:
a) 1 to 20 parts by weight of a surface modified nanoparticle component having ethylenically unsaturated groups, wherein the average particle size 20 nanometers or less; and
b) 80 to 99 parts by weight of a monomer component comprising:
a monofunctional poly(alkylene oxide) free-radically polymerizable macromonomer having a poly(alkylene oxide) moiety, optionally a multifunctional poly (alkylene oxide) free-radically polymerizable macromonomer having a poly(alkylene oxide) moiety, optionally a polar monomer, and optionally a hydrophobic monomer.

The poly(alkylene oxide) moiety is of the general formula
—(CH($R^1$)—CH$_2$—O—)$_m$—(CH$_2$—CH$_2$—O—)$_n$—,
wherein m may be 0, n is at least 1 and the mole ratio of n to m (n:m) is greater than 2:1, preferably greater than 3:1; and $R^1$ is a ($C_1$-$C_4$) alkyl group. The structural distribution of —CH ($R^1$)—CH$_2$—O— moieties and —CH$_2$—CH$_2$—O— moieties may be random or blocks. Preferably m+n is at least 5, and more preferably at least 10. Preferably m+n is less than 100, and more preferably less than 50. It will be understood that m and n may be non-integral, as the poly(alkylene oxide) moieties are generally a mixture of varying amounts or populations of the m and n units. The ethylenically unsaturated groups of the surface modified nanoparticle component improves the physical properties of the resultant cured composition, particularly in the water-swollen state. The surface modified nanoparticles copolymerize with the monomer component improving the structural integrity of the cured composition. Preferably, the surface modified nanoparticle component further comprises hydrophilic poly(alkylene oxide) groups in addition to the ethylenically unsaturated groups, which allows the nanoparticles to be easily dispersed in the monomer component, while retaining the clarity (transparency).

The monomer component of the curable composition may further comprise other polar monomers (other than the monofunctional macromonomer), multifunctional poly(alkylene oxide), and/or free-radically polymerizable macromonomer (having two or more free-radically polymerizable groups) and/or hydrophobic monomers; each discussed in more detail herein.

The present invention provides a medical article that includes a gel material derived from the cured composition including a homopolymer or copolymer of a monofunctional poly(alkylene oxide) free-radically polymerizable macromonomer having a poly(alkylene oxide) moiety.

By "gel" (or "polymer gel" or "polymeric gel material" or "hydrophilic gel") it is meant a gel material, derived from the cured composition, capable of swelling on contact with water (or water-based fluids such as body fluids including blood, plasma, and intracellular fluid or fluids similar to body fluids such as physiological saline), but does not dissolve in water.

The gels are substantially continuous, i.e., lacking a cellular or void structure (although minor defects such as entrapped air bubbles or fractures may be present) and thus generally in a solid or semi-solid form. The term "gel" is used regardless of the state of hydration. Preferably, the gel does not include water until it comes in contact with a surface from which it absorbs water (e.g., a wound). Significantly, even without water (or other plasticizing agents) preferred embodiments of the gel material of the present invention are flexible.

The application of water swelling polymer gels to medical practice is, for example, found in wound dressings, wound packings, adhesives (particularly pressure sensitive adhesives), contact lenses, intraocular lenses, adhesives for biological tissues, adhesion preventing materials, adsorbents for blood purification, base materials for releasing pharmacologic agents, and the like. Materials for dental moldings or impressions are another potential medical article use. Thus, as used herein, a "medical" application encompasses dental applications, including dental adhesives, restoratives, coatings, composites, sealants, etc. Because water swelling polymer gels have compositions and mechanical properties similar to those of biological tissues, such gels may be applied in a wide variety of fields in the future.

The present invention also provides a wound dressing that includes a facing layer (preferably, a fluid permeable facing layer) and a backing layer (preferably, a moisture vapor permeable backing layer) with the gel material (typically in the form of a layer) disposed between the two. Preferably the backing layer is both moisture vapor permeable and liquid impermeable. The medical article, e.g., wound dressing, may further include a layer of pressure sensitive adhesive to secure the article to the skin.

The composition of the present invention, which is absorbent and preferably transparent, includes a surface modified nanoparticle component having ethylenically unsaturated groups, and a polymerized, monofunctional, poly(alkylene oxide) macromonomer that, prior to polymerization, is free-radically polymerizable, monofunctional, and has at least five —$CH_2$—$CH_2$—O— repeat units, and may have —$CH(R^1)$—$CH_2$—O— repeat units, such that the macromonomer has a total of at least five, and preferably at least ten repeat units, and the ratio of —$CH_2$—$CH_2$—O— repeat units to —$CH(R^1)$—$CH_2$—O— repeat units is at least 2:1.

This gel material can be a homopolymer of the monofunctional macromonomer, or it can be a copolymer (i.e., having two or more different monomers), wherein at least one of the monomers is a monofunctional macromonomer of the above formula. Other monomers that can be copolymerized with the multifunctional macromonomer include, for example, multifunctional poly(alkylene oxide) macromonomers, polar monomers, and hydrophobic monomers.

By "absorbent" it is meant that the material is preferably capable of absorbing fluids, particularly body fluids and preferably moderate to heavy amounts of body fluids, while retaining its structural integrity (i.e., remaining sufficiently intact such that it can perform the function of acting as an absorbent moist wound healing dressing, for example), and preferably its transparency. By "transparent" it is meant that when the preferred material is applied to a patient (e.g., at a wound site), the area underlying the dressing can be visualized sufficiently to permit observation of the wound by a health care worker.

"(Meth)acryloyl" refers to both acryloyl and methacryloyl groups and includes (meth)acrylates and (meth)acrylamides.

"Curable composition" refers to the total composition including the monomer component that comprises at least one polymerizable monofunctional macromonomer and the inorganic surface-modified nanoparticles.

The term "nanoparticles" is defined herein to mean particles (primary particles or associated primary particles) with a diameter less than about 100 nm, preferably 20 nanometers or less.

"Surface modified colloidal nanoparticle" refers to nanoparticles each with a modified surface such that the nanoparticles provide a stable dispersion.

"Agglomeration" refers to a weak association between primary particles which my be held together by charge or polarity and can be broken down into smaller entities.

DETAILED DESCRIPTION

The present invention is directed to a curable composition comprising:
  a) 1 to 20 parts by weight of a surface modified nanoparticle component having ethylenically unsaturated groups and optional hydrophilic poly(alkylene oxide) groups, wherein the average particle size is 20 nanometers or less; and
  b) 80 to 99 parts by weight of a monomer component comprising:
     a monofunctional poly(alkylene oxide) free-radically polymerizable macromonomer having a poly(alkylene oxide) moiety, optionally a multifunctional poly(alkylene oxide) free-radically polymerizable macromonomer having a poly(alkylene oxide) moiety, optionally a polar monomer, and optionally a hydrophobic monomer.

The gel material, derived from the cured composition of the present invention, can be used in medical articles. The gel material is hydrophilic and absorbent. Preferably, the gel material of the present invention is advantageously transparent, which allows for inspection of an underlying material. Significantly, for medical articles, particularly wound dressings, this allows for visual inspection of the wound without removal of the wound dressing. More preferably, the gel material is both absorbent and transparent.

Preferred medical articles, particularly wound dressings, of the present invention advantageously: can remove excess exudate from the wound; maintain a moist wound environment; allow gas exchange so that oxygen, water vapor, and carbon dioxide can pass through the article; are thermally insulating to maintain the wound at body temperature; may be impermeable to liquids and microorganisms to minimize contamination and infection; may be non-adherent to the wound so that no damage is done to the granulating tissue; and minimize the need to cleanse the wound of dressing material.

The cured composition is preferably absorbent in that it is capable of absorbing fluids, preferably moderate to heavy amounts of fluids such as body fluids, while retaining its structural integrity (and preferably its transparency). Preferably, herein, "absorbent" refers to a material that will absorb at least its own weight of an isotonic saline solution (0.9 wt-% sodium chloride in deionized water) after 24 hours at room temperature. That is, the material has an absorbency of at least 100%. More preferably, the gel material can absorb at least two times its weight (200% absorbency), even more preferably at least four times its weight (400% absorbency), and most preferably at least five times its weight (500% absorbency) of an isotonic saline solution after 24 hours at room temperature. Preferably, the gel material of the present invention is transparent whether dry or swollen with an aqueous solution (e.g., bodily fluid). Preferably, herein, transparent refers to a material having a total light transmittance of greater than 85% per ASTM D1003-00.

Preferred gel materials of the present invention may be relatively flexible. Flexibility allows for a medical article incorporating the gel material to be easily applied to a bend portion of a body, such as a joint, etc. Nonflexible gel materials are also within the scope of the present invention. Such gel materials can be used as wound packing materials, for example.

The gel material of the present invention is also preferably biocompatible. Herein, "biocompatible" means that the material can be in contact with bodily tissues (including fluids) without adverse reactions. Typically, this occurs if the residual monomers used to prepare the polymer used in the gel material are present in less than about 1 percent by weight (wt-%) each, based on the total weight of the polymer.

Preferably, the polymer used in the gel material of the present invention is inherently bacteriostatic and possesses low odor. Alternatively, bacteriostatic or odor removing agents can be added to the polymer to enhance these properties of the gel material. Such materials are described in greater detail below.

The curable composition of the invention comprises a surface modified nanoparticle component having ethylenically unsaturated groups and optional hydrophilic poly(alkylene oxide) groups wherein the average particle size is 20 nanometers or less, prior to surface modification. Preferably the polydispersity of the inorganic nanoparticles is less than 2, prior to surface modification.

Nanoparticles that are surface modified in accordance with the present invention comprise nanometer-sized, inorganic oxide particles such as silica; metal oxides such as alumina, tin oxide, iron oxide, zirconia, vanadia, and titania; combinations of these; and the like. The colloidal nanoparticles can comprise essentially a single oxide such as silica or can comprise a core of an oxide of one type (or a core of a material other than a metal oxide) on which is deposited an oxide of another type. Silica is the most preferred nanoparticle. It is also preferable that the colloidal nanoparticles be relatively uniform in size and remain substantially non-aggregated, as nanoparticle aggregation can result in precipitation, gellation, or a dramatic increase in viscosity. The term "nanometer-sized" refers to particles that are characterized by an average particle diameter in the range of from about 5 nm to about 100 nm, but are preferably 20 nanometers or less, more preferably 10 nanometers or less (prior to surface modification) in the curable composition of the invention. Further, the nanoparticles generally have a surface area greater than about 150 $m^2$/gram, preferably greater than 200 $m^2$/gram, and more preferably greater than 400 $m^2$/gram.

Average particle size of the inorganic nanoparticles can be measured using transmission electron microscopy. In the practice of the present invention, particle size may be determined using any suitable technique. Preferably, particle size refers to the number average particle size and is measured using an instrument that uses transmission electron microscopy or scanning electron microscopy. Another method to measure particle size is dynamic light scattering that measures weight average particle size. One example of such an instrument found to be suitable is the N4 PLUS SUB-MICRON PARTICLE ANALYZER available from Beckman Coulter Inc. of Fullerton, Calif.

The unmodified nanoparticles may be provided as a sol rather than as a powder. Preferred sols generally contain from about 15 to about 50 weight percent of colloidal inorganic oxide particles dispersed in a fluid medium. Representative examples of suitable fluid media for the colloidal particles include water, aqueous alcohol solutions, lower aliphatic alcohols, ethylene glycol, N,N-dimethylacetamide, formamide, and combinations thereof. The preferred fluid medium is aqueous, e.g., water and optionally one or more alcohols. When the colloidal particles are dispersed in an aqueous solvent, the particles may be stabilized due to common electrical charges that develop on the surface of each particle. The common electrical charges tend to promote dispersion rather than agglomeration or aggregation, because the similarly charged particles repel one another. By contrast, fumed silica and silica gels are aggregates of fused particles and thus will not as easily provide a uniform dispersion of particles when combined with the monomer component of the curable composition. Thus, a particularly desirable class of nanoparticles for use in preparing the compositions of the invention includes sols of inorganic nanoparticles (e.g., colloidal dispersions of inorganic nanoparticles in liquid media), especially sols of amorphous silica.

Inorganic silica sols in aqueous media are well known in the art and available commercially. Silica sols in water or water-alcohol solutions are available commercially under such trade names as LUDOX (manufactured by E.I. duPont de Nemours and Co., Inc., Wilmington, Del., USA), NYACOL (available from Nyacol Co., Ashland, Mass.) or NALCO (manufactured by Nalco Chemical Co., Oak Brook, Ill. USA). One useful silica sol is NALCO 2326 available as a silica sol with mean particle size of 5 nanometers, pH 10.5, and solid content 15% by weight. Additional examples of suitable colloidal silicas are described in U.S. Pat. No. 5,126, 394, incorporated herein by reference.

The sols used in the present invention generally may include countercations, in order to counter the surface charge of the colloids. Depending upon pH and the kind of colloids being used, the surface charges on the colloids can be negative or positive. Thus, either cations or anions are used as counter ions. Examples of cations suitable for use as counter ions for negatively charged colloids include $Na^+$, $K^+$, $Li^+$, a quaternary ammonium cation such as $NR_4^+$, wherein each R may be any monovalent moiety, but is preferably H or lower alkyl such as $CH_3$—, combinations of these, and the like. Examples of counter anions suitable for use as counter ions for positively charged colloids include nitrate, acetate, chloride, etc.

A variety of methods are available for modifying the surface of nanoparticles including, e.g., adding a surface modifying agent to nanoparticles (e.g., in the form of a powder or a colloidal dispersion) and allowing the surface modifying agent to react with the nanoparticles. Other useful surface modification processes are described in, e.g., U.S. Pat. No. 2,801,185 (Iler), U.S. Pat. No. 5,648,407 (Goetz et al.) and U.S. Pat. No. 4,522,958 (Das et al.), each incorporated herein by reference.

Surface modifying agents that may be used to provide an ethylenically unsaturated group to the surface of the inorganic nanoparticles may be represented by the formula $X_p$—$R^3$—$Y_q$ (I), wherein:

X represents a functional group that may bond to, or associate with, the surface of the inorganic nanoparticles, and is preferably selected from a silyl, hydroxyl, azido, mercapto, alkoxy, nitro, cyano, or amino group. Preferably X is a functional group that forms a covalent bond with the surface functional groups of the inorganic nanoparticles, e.g. a reactive functional group that forms a covalent bond with the Si—OH groups on the surface of silica nanoparticles.

$R^3$ is a covalent bond or polyvalent hydrocarbon bridging group of valence p+q. In one embodiment $R^3$ is a polyvalent hydrocarbon bridging group of about 1 to 20 carbon atoms, including alkylene and arylene and combinations thereof, optionally including in the backbone 1 to 5 moieties selected from the group consisting of —O—, —C(O)—, —S—, —SO$_2$— and —NR$^2$— groups (an combinations thereof such as —C(O)—O—), wherein R$^2$ is hydrogen, or a C$_1$-C$_4$ alkyl group. In another embodiment, R$^3$ is a poly(alkylene oxide) moiety. Preferably, R$^3$ is a divalent alkylene.

Y is an ethylenically unsaturated polymerizable group, including vinyl, allyl, vinyloxy, allyloxy, and (meth)acryloyl, and p and q are independently 1 to 4, preferably 1.

Preferred surface modifying agents include those with the following formula:

$$Y\text{—}R^3\text{—}Si\text{—}(OR^4)_b(R^4)_{3-b} \qquad \text{II}$$

wherein:

R$^3$ is a covalent bond or a polyvalent hydrocarbon bridging group of valence p+q. In one embodiment R$^3$ is a polyvalent hydrocarbon bridging group of about 1 to 20 carbon atoms, including alkylene and arylene and combinations thereof, optionally including in the backbone 1 to 5 moieties selected from the group consisting of —O—, —C(O)—, —S—, —SO$_2$— and —NR$^2$— groups (and combinations thereof such as —C(O)—O—), wherein R$^2$ is hydrogen, or a C$_1$-C$_4$ alkyl group. In another embodiment, R$^3$ is a poly(alkylene oxide) moiety of the formula —(OCH$_2$CH$_2$—)$_n$(OCH$_2$CH(R$^1$))$_m$—, where wherein n is at least 5, m may be 0, and preferably at least 1, and the mole ratio of n:m is at least 2:1 (preferably at least 3:1).

Preferably, R$^3$ is a divalent alkylene.

Y is an ethylenically unsaturated polymerizable group, including vinyl, allyl, vinyloxy, allyloxy, and (meth)acryloyl, R$^4$ is independently an alkyl, aryl, or aralkyl group of 1 to 8 carbon atoms optionally substituted in available positions by oxygen, nitrogen and/or sulfur atoms; and b is 1 to 3.

Useful surface modifying agents that may be used to functionalize the nanoparticles with ethylenically unsaturated groups includes organosilanes such as, for example, 3-(methacryloyloxy)propyltrimethoxysilane, 3-acryloxypropyltrimethoxysilane, 3-(methacryloyloxy)propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)propyldiethylethoxysilane, vinyldimethylethoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri-t-butoxysilane, vinyltrisisobutoxysilane, vinyltriisopropenoxysilane, vinyltris(2-methoxyethoxy)silane, and mixtures thereof.

The ethylenically unsaturated surface modifying agent is used in amounts sufficient to react with at least 10%, preferably 10% to 90%, of the available functional groups on the inorganic nanoparticle (for example the number of available Si—OH groups on silica nanoparticles). The number of functional groups is experimentally determined where a quantity of nanoparticles are reacted with an excess of surface modifying agent so that all available reactive sites are functionalized with a coupling agent. Lower percentages of functionalization may then be calculated from the result.

The multifunctionality of the surface modified nanoparticles leads to crosslinking with the component monomers upon polymerization so that the nanoparticles are chemically bound to the cured composition. Typically, the higher the degree of functionalization, the higher the crosslink density, leading to better mechanical properties. That is, the materials of the present invention possess an advantageous balance of compliance (i.e., elasticity) and tensile strength as well as cohesive strength in the swollen form as a result of the use of the ethylenically unsaturated surface modified functional groups.

The nanoparticles of the invention may be further modified to provide a plurality of hydrophilic poly(alkylene oxide) groups thereto. The hydrophilic poly(alkylene oxide) groups comprise the moiety:

$$\text{—Q—(CH(R}^1\text{)—CH}_2\text{—O—)}_m\text{—(CH}_2\text{—CH}_2\text{—O—)}_n\text{—R}^2 \qquad \text{III}$$

wherein n is at least 5, m may be 0, and preferably at least 1, and the mole ratio of n:m is at least 2:1 (preferably at least 3:1);

Q is —O—, —S— or —NR$^2$—, R$^1$ is a (C$_1$-C$_4$) alkyl group, which can be linear or branched, and R$^2$ is R$^1$ or H.

The distribution of the alkylene oxide moieties may be random (i.e., there is a relatively random structural distribution of at least two different moieties) or block.

In one embodiment, the nanoparticles may be functionalized by means of a ambiphilic coupling agent capable of bonding a poly(alkylene oxide) compound to the nanoparticles.

The ambiphilic coupling agent has at least two reactive functional groups. The first reactive functional group is capable of covalently bonding to the surface of the nanoparticles and the second reactive functional group is capable of bonding to the poly(alkylene oxide) compound. For example, reactive functionalities such as amino, hydroxyl, mercaptan, or isocyanate groups present on one component (the poly(alkylene oxide) compound, coupling agent, or the particles) can react with complementary reactive functionalities, such as oxirane, chloro-, bromo-, iodo-, alkyl, aziridine, anhydride, or isocyanato groups, present on the other component (coupling agent or poly(alkylene oxide) compound). More than one coupling agent may be used.

The poly(alkylene oxide) compound is of the formula $$Z\text{—(CH(R}^1\text{)—CH}_2\text{—O—)}_m\text{—(—CH}_2\text{—CH}_2\text{—O—)}_n\text{—R}^2 \qquad \text{IV}$$

wherein Z is a functional group, reactive with the second functional group of the ambiphilic coupling agent, such as a hydroxyl, amino, thio, or isocyanate.

R$^1$ is a C$_1$ to C$_4$ alkyl group,

R$^2$ is a R$^1$ or H.

Preferably R$^1$ is a methyl and the poly(alkylene oxide) moiety is a poly(ethylene oxide-co-propylene oxide) where m and n are at least 1, m'+n is at least five, and n:m is at least 2:1. It will be understood that the poly(alkylene oxide) group may be random or block.

Useful ambiphilic silane coupling agents include those with the following formula:

$$FG^2{}_a\text{-R}^3\text{—Si—(OR}^4)_b(R^4)_{3-b} \qquad (V)$$

wherein:

FG$^2$ is the second reactive functional group of the ambiphilic coupling agent capable of reacting with complementary functionalities of the Z group of the poly(alkylene oxide) compound of Formula IV. Examples of FG$^2$ include amino; hydroxyl; mercaptan; epoxy; chloro-, iodo-, and bromoalkyl; aziridine; cyclic carboxylic anhydride; hydrogen and isocyanato groups.

R$^3$ is a covalent bond or a polyvalent hydrocarbon bridging group of valence p+q. In one embodiment R$^3$ is a polyvalent hydrocarbon bridging group of about 1 to 20 carbon atoms, including alkylene and arylene and combinations thereof, optionally including in the backbone 1 to 5 moieties selected from the group consisting of —O—, —C(O)—, —S—, —SO$_2$— and —NR$^2$— groups (an combinations thereof such as —C(O)—O—), wherein $R^2$ is hydrogen, or a $C_1$-$C_4$ alkyl group. In another embodiment, $R^3$ is a poly(alkylene oxide) moiety of the formula —(OCH$_2$CH$_2$—)$_n$(OCH$_2$CH(R$^1$))$_m$—, where wherein n is at least 5, m may be 0, and preferably at least 1, and the mole ratio of n:m is at least 2:1 (preferably at least 3:1).

$R^4$ is independently an alkyl, aryl, or aralkyl group of 1 to 8 carbon atoms optionally substituted by catenary oxygen, nitrogen and/or sulfur atoms;

a is 1 or 2; and b is 1 to 3;

$FG^2$ and Z are generally selected so that one is nucleophilic and the other is electrophilic. Examples of pairs of complementary, or co-reactive, functional groups $FG^2$ and Z include isocyanate, epoxy or anhydride groups with nucleophilic functional groups such as hydroxyl, amino or mercapto. Alternatively, FG2 may be a hydrogen of a silicon hydride, and Z may be a vinyl group.

It should be understood that when present in the compositions of the invention the coupling agents may hydrolyze, in which case one or more of the "OR$^4$" groups will be converted to a silanol or silanolate.

Preferred ambiphilic silane coupling agents have the structure $FG^2$-$R^3$—Si(OR$^4$)$_3$ wherein $FG^2$ is preferably an isocyanate group, and $R^3$ and $R^4$ are as described above.

Additional information on ambifunctional silane coupling agents may be found in U.S. Pat. No. 5,204,219, issued to Van Ooij et al., U.S. Pat. No. 5,464,900, issued to Stofko et al., and U.S. Pat. No. 5,639,546, issued to Bilkadi and European Patent Application No. 0,372,756 A2. Alternatively the coupling agent can be a titanate or zirconate compound, such as "Tyzor™ Titanate, 11 commercially available from DuPont.

Alternatively, the poly(alkylene oxide) compound of the formula IV and the ambiphilic coupling agent V are reacted together prior to surface modification of the inorganic nanoparticles. In this instance, the reaction may result in an PEG functionalized silane of the formula:

$$R^2—(OCH_2CH_2—)_n(OCH_2CH(R^1))_m—Q'-R^3—Si—(OR^4)_b(R^4)_{3-b} \quad (VI)$$

wherein Q' is a divalent linking group resulting from the reaction between the "Z" group of the poly(alkylene oxide) compound of Formula IV and the "FG$^2$" group of the ambiphilic silane coupling agent of Formula V. For example, where FG$^2$ is an isocyanate and Z is a hydroxyl, Q' will be a urethane link.

$R^1$ is a $C_1$ to $C_4$ alkyl group, $R^2$ is a $R^1$ or H, $R^3$ is a polyvalent hydrocarbon bridging group. In one embodiment $R^3$ is a polyvalent hydrocarbon bridging group of about 1 to 20 carbon atoms, including alkylene and arylene and combinations thereof, optionally including in the backbone 1 to 5 moieties selected from the group consisting of —O—, —C(O)—, —S—, —SO$_2$— and —NR$^2$— groups (an combinations thereof such as —C(O)—O—), wherein $R^2$ is hydrogen, or a $C_1$-$C_4$ alkyl group. In another embodiment, $R^3$ is a poly(alkylene oxide) moiety. Preferably, $R^3$ is a divalent alkylene.

$R^4$ is independently an alkyl, aryl, or aralkyl group of 1 to 8 carbon atoms optionally substituted by catenary oxygen, nitrogen and/or sulfur atoms;

n is at least 5, m may be 0, and preferably at least 1, and the mole ratio of n:m is at least 2:1 (preferably at least 3:1); and b is 1 to 3.

Less preferably the nanoparticles are first reacted with the ambiphilic coupling agent of Formula V, then further reacted with the poly(alkylene oxide) compound of Formula IV, as the efficiency of functionalization of the inorganic nanoparticles is reduced.

The ambiphilic coupling agent, whether the coupling agent V is used per se, or the poly(alkylene oxide) coupling agent (VI), is used in amounts sufficient to react with all or part of the available surface functional groups on the inorganic nanoparticle, i.e those surface functional groups remaining after functionalization by the ethylenically unsaturated surface modifying agent of Formulas I or II. The number of functional groups is experimentally determined where a quantity of nanoparticles are reacted with an excess of coupling agent so that all available reactive sites are functionalized with a coupling agent. Lower percentages of functionalization may then be calculated from the result. The functionalization of the inorganic nanoparticles may be sequential or concurrent. The inorganic nanoparticles may first be functionalized by the surface modifying agent of Formulas I or II, followed by functionalization by surface modifying agents of Formulas V (followed by reaction with the compound of Formula IV), or the surface modifying agent of Formula VI. Alternately the surface of the nanoparticles may be simultaneously modified by both the ethylenically unsaturated groups and the poly (alkylene oxide) groups.

The monomer component of the instant curable composition comprises one or more monofunctional poly(alkylene oxide) monomers to increase the hydrophilicity and absorbency of the cured composition used in forming the gel material. The monomers comprise one terminal polymerizable ethylenically unsaturated group (e.g., only one (meth)acryloyl group, vinyl group, allyl group or allyloxy group), a poly(alkylene oxide) moiety (such as previously described) and a second, non-polymerizable, terminal end group such as H, (C$_1$-C$_4$) alkoxy, aryloxy (e.g., phenoxy), or (C$_1$-C$_4$) alkaryloxy groups. These groups can be linear or branched.

Preferred monofunctional poly(alkylene oxide) monomers are of the formula:

$$R^6—Q—(CH(R^1)—CH_2—O—)_m—(CH_2—CH_2—O—)_n—R^2 \quad VII$$

wherein $R^6$ is a ethylenically unsaturated polymerizable group, including vinyl, allyl, vinyloxy, allyloxy, and (meth)acryloyl, $R^1$ is a (C$_1$-C$_4$) alkyl group, $R^2$ is H or $R^1$, Q is —O—, —S— or —NR$^2$—, n is at least 5, m may be 0, and preferably at least 1, n+m is at least 5 and preferably at least 10, and the mole ratio of n:m is at least 2:1 (preferably at least 3:1).

Preferably $R^6$ is selected from the groups consisting of:

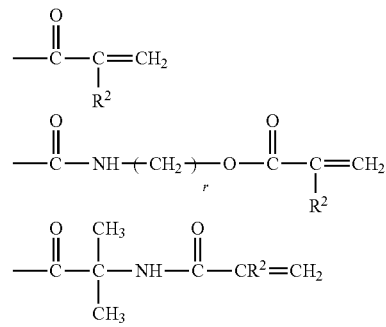

-continued

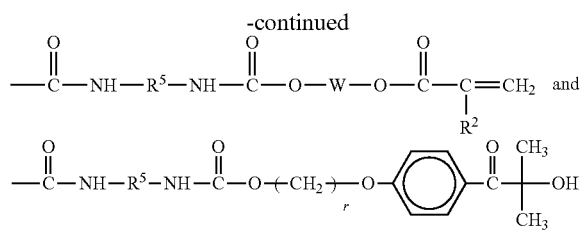

wherein $R^2$ is H or $C_1$-$C_4$ alkyl,
$R^5$ is an aromatic group, aliphatic group, alicyclic group, or combinations thereof,
W is an alkylene or alkylene oxide group, and r=2-10. Preferably $R^6$ is (meth)acryloyl.

Examples of suitable monofunctional poly(alkylene oxide) monomers include poly(ethylene oxide)(meth)acrylate, poly(propylene oxide)(meth)acrylate, poly(ethylene oxide-propylene oxide)(meth)acrylate, and combinations thereof. Such monomers typically include nonreactive end groups (to free-radically polymerizations) such as ($C_1$-$C_4$) alkoxy, aryloxy (e.g., phenoxy), ($C_1$-$C_4$) alkaryloxy, aryl($C_1$-$C_4$) alkyloxy, or hydroxy groups. These groups can be linear or branched. These monomers can be of a wide range of molecular weights and are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

The monofunctional macromonomers can be prepared, for example, by reacting monohydroxy terminated alkylene oxide homo- or copolymers (which are typically commercially available) with reactive ethylenically unsaturated compounds (e.g., acrylates).

A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl (meth)acrylate. In addition, the monohydroxy terminated alkylene oxide random copolymer can be reacted with a diisocyanate, such as isophorone diisocyanate, resulting in an isocyanate terminated functional random copolymer that is further reacted with either functional (meth)acrylates. Preferably, the monofunctional macromonomer is prepared by reacting the hydroxy terminated poly(alkylene oxide) compound with acrylic acid. Typically, if a stoichiometric amount of the ethylenically unsaturated reactant is combined with the monohydroxy terminated alkylene oxide random copolymer, 100% conversion to the monosubstituted product is obtained.

The curable composition of the present invention optionally includes a multifunctional poly(alkylene oxide) free-radically polymerizable macromonomer. The monomers comprise two or more terminal polymerizable ethylenically unsaturated group (e.g., (meth)acryloyl group, vinyl group, or allyl group), and a poly(alkylene oxide) moiety (as previously described). The multifunctional poly(alkylene oxide) macromonomer preferably has a weight average molecular weight of at least about 2000. Preferably, the multifunctional poly(alkylene oxide) macromonomer includes a alkylene oxide moiety of the formula —(CH($R^1$)—$CH_2$—O—)$_m$—($CH_2$—$CH_2$—O—)$_n$—, wherein m may be 0, n is at least 1 and the mole ratio of n to m (n:m) is greater than 2:1, preferably greater than 3:1; and $R^1$ is a ($C_1$-$C_4$) alkyl group.

The multifunctionality of the material leads to crosslinking upon polymerization. Typically, the higher the molecular weight, the greater the distance between crosslinks (i.e., the lower the crosslink density), which leads to better mechanical properties. That is, the materials of the present invention possess an advantageous balance of compliance (i.e., elasticity) and tensile strength as well as cohesive strength in the swollen form as a result of the use of the multifunctional poly(alkylene oxide) macromonomer.

The multifunctional macromonomer preferably may have a weight average molecular weight of at least about 2000. Macromonomers with molecular weights lower than this tend to form brittle polymers. Preferably the multifunctional macromonomer has a weight average molecular weight of at least about 4000, more preferably at least about 6000, and most preferably at least about 10,000. Such materials can have significantly higher molecular weights as well. Preferably, such multifunctional macromonomers have a molecular weight such that they are flowable and processable at room temperature. High molecular weight multifunctional macromonomers that are not flowable at room temperature can be used if they can be processed using diluents or other additives and/or higher temperatures (e.g., extrusion temperatures). Most preferably, useful multifunctional macromonomers are liquid at room temperature.

Herein, multifunctional means that the macromonomer has more than one reactive group that is free radically polymerizable. Preferably, there are two or three reactive groups, and more preferably two reactive groups. Such multifunctional macromonomers can be linear or branched, preferably they are linear.

Preferably, the free radically polymerizable functionality of the multifunctional macromonomer includes ethylenic unsaturation. Examples of suitable ethylenically unsaturated groups include (meth)acryloyl, (meth)acrylamido, allyloxy, vinyl, etc., as well as combinations thereof.

Preferably, the multifunctional macromonomer is difunctional. A particularly preferred difunctional macromonomer is of the formula (Formula VIII):

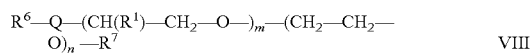

wherein:
$R^6$ and $R^7$ are each independently an ethylenically unsaturated polymerizable group, including vinyl, allyl, vinyloxy, allyloxy, and (meth)acryloyl,
$R^1$ is a ($C_1$-$C_4$) alkyl group,
$R^2$ is H or $R^1$,
Q is —O—, —S— or —$NR^2$—,
n is at least 5, m may be 0, and preferably at least 1, n+m is at least 5, and preferably at least 10, and the mole ratio of n:m is at least 2:1 (preferably at least 3:1).

Preferably $R^6$ and $R^7$ are each independently selected from the groups consisting of

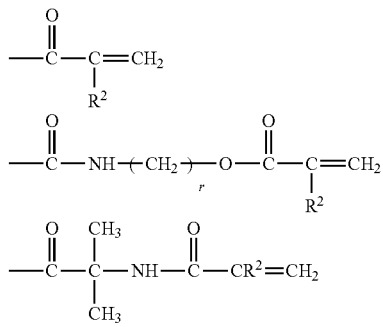

-continued

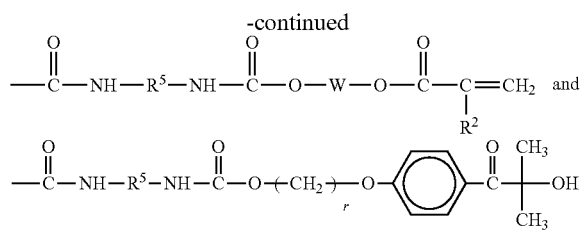

wherein
$R^1$ is a $C_1$ to $C_4$ alkyl,
$R^2$ is H or $R^1$,
$R^5$ is an aromatic group, aliphatic group, alicyclic group, or combinations thereof,
W is an alkylene or alkylene oxide group, and r=2-10. Preferably $R^6$ and $R^7$ are (meth)acryloyl.

Preferably, the $R^5$ groups are derived from diisocyanates. More preferably, $R^5$ is selected from the group consisting of —$(CH_2)o$—wherein o=1-18, tolylene, and

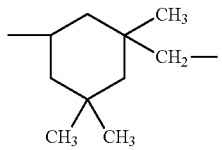

Most preferably, $R^5$ is derived from toluene diisocyanate, hexamethylene diisocyanate, or $H_{12}$-MDI (4,4'-methylene bis(cyclohexyl)diisocyanate).

Preferably, W is a $C_2$ to $C_{20}$ alkylene or a poly(alkylene oxide) moiety of of the general formula —$(CH(R^1)$—$CH_2$—$O$—$)_m$—$(CH_2$—$CH_2$—$O$—$)_n$—, wherein m may be 0, n is at least 1 and the mole ratio of n to m (n:m) is greater than 2:1, preferably greater than 3:1; and $R^1$ is a $(C_1$-$C_4)$ alkyl group. The poly(alkylene oxide) moieties of Formula VII may be random or block. More preferably, it is a random poly(ethylene oxide-co-propylene oxide)-containing multifunctional macromonomer.

The multifunctional macromonomers can also be tri-, tetra-, penta-functional, etc., macromonomers. Such compounds also include a poly(alkylene oxide) moiety of Formula I, wherein n is at least 5, m is 0 and preferably at least 1, m+n is at least 5 and preferably at least 10, and the ratio of n to m is at least 2:1, preferably at least 3:1; and $R^1$ is a methyl group, and two or more end groups selected from the list of $R^6$ and $R^7$ groups above. It should be understood that such end groups may be bonded through oxygen or nitrogen.

Multifunctional macromonomers can be linear with branched end groups or can be branched through a central core. Branched macromonomers can be prepared, for example, by chemical modification of linear diamino- or dihydroxy terminated alkylene oxide random copolymers to produce multiple reactive end groups at each chain end. For example, a macromonomer with two polymerizable groups at each chain end can be prepared by reacting a linear diamino- or dihydroxy terminated poly(alkylene oxide) compound with trimellityl chloride followed by reaction with 2-hydroxyethyl methacrylate. Branch points in the macromonomer can also be introduced through incorporation of a central core. Examples of such materials include, but are not limited to, ethoxylated/propoxylated dipentaerythritol, pentaerythritol, and trimethyolpropane that have been further reacted with reactive ethylenically unsaturated compounds.

It should also be understood that each arm of a multifunctional macromonomer includes the copolymeric random alkylene oxide moiety, although each arm in any one macromonomer can be different. Also, there can be other groups or linkages, such as urethanes and/or urea groups between various copolymeric random alkylene oxide moieties in any one arm.

The multifunctional macromonomers can be prepared, for example, by reacting diamino- or dihydroxy-terminated poly(alkylene oxide) compound (which are typically commercially available such as poly(ethylene oxide-co-propylene oxide) commercially available as UCON-75H-90,000 from Dow Chemical Co., Midland, Mich.) with reactive ethylenically unsaturated compounds (e.g., acrylates). A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl(meth)acrylate. In addition, the diamino- or dihydroxy-terminated poly(alkylene oxide) compound can be reacted with a diisocyanate, such as isophorone diisocyanate, resulting in an isocyanate terminated functional random copolymer that is further reacted with either functional (meth)acrylates.

Preferably, the functional macromonomer is prepared by reacting the diamino- or dihydroxy-terminated poly(alkylene oxide) compound with methacrylic anhydride. Typically, if a stoichiometric amount of the ethylenically unsaturated reactant is combined with the diamino- or dihydroxy terminated poly(alkylene oxide) compound, 100% conversion to the disubstituted product is obtained. However, if less than a stoichiometric amount is used, the product is typically a mixture of disubstituted and monosubstituted products and possibly some diamino- or dihydroxy terminated starting material. Such mixtures tend to provide gels with higher absorbency.

A multifunctional macromonomer as described herein can be copolymerized with the monofunctional macromonomers or other hydrophilic monomers to enhance the absorbency of the polymer used in forming the gel material. Examples of suitable hydrophilic monomers include monofunctional poly(alkylene oxide) monomers and other polar monomers. The multifunctional macromonomer (or combination of macromonomers) can be copolymerized with hydrophobic monomers also to better control the absorbency of the polymer. Combinations of such hydrophilic and hydrophobic monomers can be used if desired.

Polar monomers other than the mono- and multifunctional poly(alkylene oxide) macromonomers can also be used to increase the absorbency of the polymer used in forming the gel material. Preferred polar monomers can also provide compliance to the resultant polymer. Examples of suitable polar monomers include 2-hydroxyethyl(meth)acrylate (HEMA), 2-hydroxypropyl(meth)acrylate, 3-hydroxypropyl (meth)acrylate, 4-hydroxybutyl(meth)acrylate, N-vinyl caprolactam, N-vinyl acetamide, N-vinyl pyrrolidone, acrylamide, mono- or di-N-alkyl substituted acrylamide, (meth) acrylic acid, itaconic acid, beta-carboxyethyl acrylate, glycerol methacrylate, [2-(meth)(acryloyloxy)ethyl] trimethylammonium chloride, [2-(meth)(acryloyloxy)ethyl] trimethylammonium methyl sulfate, and combinations thereof. Preferred polar monomers include 2-hydroxyethyl (meth)acrylate (HEMA) and N-vinyl pyrrolidone.

Hydrophobic monomers can be used to reduce (and thereby better control) the absorbency of the polymer used in forming the gel material, and preferably improve the strength of the polymer. Examples of suitable hydrophobic monomers include (meth)acrylic acid esters such as lauryl acrylate, 2-ethylhexyl acrylate, and isooctyl acrylate, as well as alpha-methylstyrene, and combinations thereof.

Monomers used in forming the monomer component of the present invention preferably include no greater than about 80 wt-% of a monofunctional poly(alkylene oxide) monomer, based on the total weight of the monomer component. More preferably, the monofunctional poly(alkylene oxide) monomer is used in an amount of at least about 30 wt-%, based on the total weight of the polymer. Most preferably, the monofunctional poly(alkylene oxide) monomer is used in an amount of at least about 40 wt-%, based on the total weight of the polymer.

Monomers used in forming the monomer component of the present invention may include at least about 0.1 wt-% of the optional multifunctional poly(alkylene oxide) macromonomer, based on the total weight of the monomer component. Preferably, the monomer component include at least about 5 wt-% of the multifunctional poly(alkylene oxide) macromonomer, based on the total weight of the polymer. More preferably, the multifunctional poly(alkylene oxide) macromonomer is used in an amount of no greater than about 20 wt-%, based on the total weight of the monomer component.

Preferred monomers used in forming the monomer component of the present invention include no greater than about 40 wt-% of an optional polar monomer, based on the total weight of the monomer component. More preferably, the polar monomer is used in an amount of no greater than about 35 wt-%, based on the total weight of the monomer component. Most preferably, the polar monomer is used in an amount of no greater than about 30 wt-%, based on the total weight of the monomer component. Preferably, the polar monomer is used in an amount of at least about 5 wt-%, based on the total weight of the monomer component. More preferably, the polar monomer is used in an amount of at least about 10 wt-%, based on the total weight of the monomer component.

Preferred monomers used in forming the monomer component of the present invention include no greater than about 20 wt-% of an optional hydrophobic monomer, based on the total weight of the monomer component. More preferably, the hydrophobic monomer is used in an amount of less than 20 wt-%, based on the total weight of the monomer component. Even more preferably, the hydrophobic monomer is used in an amount of no greater than about 10 wt-%, based on the total weight of the monomer component. Most preferably, the hydrophobic monomer is used in an amount of no greater than about 5 wt-%, based on the total weight of the monomer component.

The monomers used in forming the monomer component of the present invention are preferably substantially acid free. By this it is meant that no acidic monomers (e.g., (meth)acrylic acid, itaconic acid) are used in preparing the polymer in the gel material, although there may be certain acidic monomers present as contaminants in other monomers used. Thus, "substantially acid free" means that less than about 2 wt-% of the monomers used to prepare the polymer are acidic monomers.

The curable composition of the present invention may be prepared by combining the surface modified inorganic nanoparticle component and the monomer component. The components, including the component monomers and the surface modified nanoparticle component, may be combined in any order. Generally the inorganic nanoparticles are surface modified, then combined with the monomer component rather than modifying the inorganic nanoparticles in situ.

It has been found that modifying the inorganic nanoparticles with poly(alkylene oxide) groups (in addition to the ethylenically unsaturated groups) prior to combining with the monomer component improves the compatibility and resultant transparency of the curable composition and gels. In the absence of poly(alkylene oxide) surface modifying groups on the surface of the inorganic nanoparticles, it is preferred to combine the surface modified nanoparticle component and the polar monomer prior to addition of the monofunctional macromonomer and multifunctional macromonomer. First combining the surface modified nanoparticle component and the monofunctional macromonomer may lead to cloudiness and reduced transparency, and is therefore less preferred.

The gel, or cured compositions, may be produced by polymerizing the above-described components (I.e. the surface modified nanoparticle component and the mononomer component) by conventional polymerization methods. Typical polymerization methods that can be used include thermal and/or photochemical as well as bulk and solution polymerization.

In a typical solution polymerization method, a monomer component and surface modified nanoparticle component are heated with stirring in the presence of a solvent and a polymerization initiator. Examples of the solvent are methanol, ethanol, isopropanol, acetone, methyl ethyl ketone, methyl acetate, ethyl acetate, toluene, xylene, and an ethylene glycol alkyl ether. Those solvents can be used alone or as mixtures thereof. Examples of the polymerization initiator are benzoyl peroxide, cumene hydroperoxide, diisopropyl peroxydicarbonate, and azobisisobutyronitrile. Those polymerization initiators can be used alone or as mixtures thereof.

In a typical photopolymerization method, a mixture of the monomer component and surface modified nanoparticle component is irradiated with ultraviolet (UV) rays in the presence of a photopolymerization initiator (i.e., photoinitiators). Preferred photoinitiators are those available under the trade designations IRGACURE from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (IRGACURE 1173). Particularly preferred photoinitiators are IRGACURE 819 and 2959.

A particularly preferred method of forming the cured composition is described in U.S. Pat. No. 6,960,275 (Vesley et al.).

Preferably, the method involves a "syrup polymer" technique, by which the monofunctional macromonomer and surface modified nanoparticle component are dissolved or dispersed in the component monomers, which react into the polymer backbone, further increasing the molecular weight. Molecular weight may be controlled through the use of chain transfer agents and chain retarding agents, as are known in the art, uch as alkyl mercaptans such as dodecyl mercaptan, isooctyl thioglycolate, and alpha-methylstyrene.

Thus, the present invention also provides a syrup polymer mixture and the polymerized product thereof. The syrup polymer mixture comprises 1 to 20, preferably 1 to 10 parts by weight of a surface modified nanoparticle component and 80 to 99 parts, preferably 90 to 99 parts by weight of a monomer mixture comprising: 30 to about 80 wt-% of a monofunctional poly(alkylene oxide) monomer; 0 to about 40 wt-% of a polar monomer (distinct from the monofunctional poly(alkylene oxide) monomer); 0 to about 20 wt-% of a hydrophobic monomer: about 0 wt-% to 20 wt-% of a multifunctional poly(alkylene oxide) macromonomer. Such a syrup is preferably partially polymerized (typically, about 10-15% conversion) to form a coatable composition (typically, having a viscosity of about 300 centipoise to about 20,000 centipoise), then coated onto a backing or a release liner, for example, and then polymerized further to form a gel. The syrup polymer mixture preferably includes a photoinitiator. The step of forming a gel from the syrup polymer mixture preferably includes applying radiation (infrared, ultraviolet, visible, electron beam, etc., preferably, ultraviolet radiation), thermal energy, or a combination thereof (preferably sequentially).

The gel material, derived from the cured composition of the present invention, can include one or more active agents, such as pharmacologically active agents. Examples include, but are not limited to, growth factors (e.g., TGF, FGF, PDGF, EGF, etc.), antibacterial agents (e.g., penicillins, neomycin sulfate, sulphonamides, sulfadiazine, silver sulfadiazine, trimethoprim, and other antibiotics, as well as povidone iodine, iodine, silver, silver chloride, and chlorhexidine), antifungal agents (e.g., griseofulvin, chlormidazole hydrochloride, clotrimazole, ketoconazole, miconazole, miconazole nitrate, nistatin, and tolnaftate), disinfectants and antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan), local anaesthetics (e.g., tetracaine, benzocaine, prilocaine, procaine), debriding agents, anti-inflammatory agents (e.g., indomethacin, ketoprofen, dichlofenac, ibuprofen, etc.), astringents, enzymes, nutrients (e.g., vitamins, minerals, oxygen, etc.), drugs for cataplasms (e.g., menthol, camphor, peppermint, capsicum extract, capsaicin, etc.), and odor absorbing agents (e.g., zeolites, silicates, chitosans, cyclodextrins, etc.). Preferred active agents are antibacterial agents such as povidone iodine, iodine, silver, silver chloride, and chlorhexidine. Active agents can be used alone or as mixtures thereof. They can be added before or after the reaction product of this invention is cured as long as they do not interfere with polymerization of the polymer. Preferably, they are added in an amount or manner that does not interfere with the function or clarity of the finished gel material.

Optionally, the gel material can include hydrocolloids, typically in the form of particles, although they are not necessarily preferred since they can diminish the transparency of the gel material. Examples of hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids. The term hydrocolloid is used regardless of the state of hydration. The gel material of the present invention preferably includes an amount of the hydrocolloid such that the material is transparent (preferably, the total light transmittance is greater than 85% per ASTM D1003-00). Typically, the amount of hydrocolloid, if used, is less than about 5 wt-%, based on the total weight of the gel material.

Other additives that can be incorporated into the cured composition include: viscosity modifiers (e.g., polymeric thickeners such as that commercially available under the trade designation GANTREZ resin from International Specialty Products, Wayne, N.J.); chain transfer or retarding agents (e.g., such as alkyl mercaptans such as dodecyl mercaptan, isooctyl thioglycolate, and a-methylstyrene, the latter of which can also be a hydrophobic monomer as discussed above); colorants; indicators; tackifiers; plasticizers (e.g., water, glycerin, polyethylene oxide, polypropylene oxide, and mixtures thereof such as those commercially available under the trade designation PLURONICS from BASF Co., as well as various low molecular compounds capable of plasticizing the polymer); antioxidants; etc. Such additives can be added either before or after the polymerization using techniques known to one of skill in the art. Preferably, if used, they can be added in an amount and manner that does not interfere with the function or clarity of the gel material.

Preferably, the cured composition is substantially free of plasticizers, including water. This is advantageous at least because special packaging is not required. Furthermore, plasticizers can migrate to other parts of a dressing, for example, which can be detrimental to the integrity of the dressing, or into the body of the patient on which the dressing is disposed.

Optionally, the gel material, derived from the cured composition, may have a patterned surface on at least one major surface thereof. The patterned surface allows greater surface area for absorption of wound exudate when oriented toward the wound surface, while reducing the absorbent surface area in direct or indirect contact with the wound. More significantly, the patterned surface reduces the propensity of the absorbent layer to swell and push against the wound, avoids mushrooming (i.e. expansion of the gel layer through a porous film) and further avoids premature separation of an adhesive layer from the skin.

The optional pattern imparted to the surface of a layer of the gel material may be any suitable preselected three-dimensional pattern. Preferably, the pattern is one that increases the surface area available for absorption and reduces swelling into the wound, retards mushrooming, and/or enhances integrity of the material upon hydration. The pattern can include an array of pattern elements that include, but are not limited to, ridges, channels, mounds, peaks, hemispheres, pyramids, cylinders, cones, blocks, and truncated variations and combinations thereof. The pattern may further include apertures having a predetermined shape and size extending through the thickness of the absorbent layer.

The specific pattern element is advantageously chosen to present minimal surface area in contact with a wound or the facing film if present. The minimal surface area further retards the tendency of the gel material to swell into the wound, mushroom, or adhere to the wound site. Especially useful elements include pyramids, cones and truncated versions thereof, and ridges that are triangular in cross section. The elements may be random or non-random in the x direction, the y direction, or both. For ease of manufacture, it is preferable that the pattern comprises a non-random array of elements disposed on the surface of the gel.

If desired, a pattern may also be imparted to the outer face of the gel layer (i.e., the major surface of the gel layer that faces away from the wound surface). Imparting such a pattern increases the surface area of the gel layer and may promote greater evaporation of the fluid from the gel material. The pattern may be the same or different than the pattern on the facing surface of the gel material, as can the size of the pattern elements. Further, the individual elements on either surface of the gel material may be protuberances extending form the surface, or may be depressions in the surface.

If desired, the gel material may be in direct contact with the wound and/or skin surface. However, direct contact may be provided by other suitable hydrocolloid and hydrogel absorbent materials.

In a preferred medical article, the gel material forms a layer that is generally about 250 micrometers (i.e., microns) to about 5000 micrometers in total thickness.

Optionally, a wound dressing of the invention may include at least two absorbent layers: a first absorbent layer and a second absorbent layer. The first absorbent layer is typically more absorbent than the second absorbent layer, and can retain a greater volume of body fluids than the second absorbent layer. The second absorbent layer is positioned such that it is located between the first absorbent layer and the wound. This second absorbent layer provides integrity to the wound dressing and avoids transfer of the first absorbent layer into the wound.

The first absorbent layer typically contains the polymer described above prepared from the multifunctional macromonomer. The second absorbent layer is typically positioned in contact with the first absorbent layer and is typically less absorbent of body fluids than the first absorbent layer. The second absorbent layer can contain the reaction product of an acrylic acid ester of a non-tertiary alcohol having from 4 to 14 carbon atoms; a hydrophilic, ethylenically unsaturated monomer; and a polar, ethylenically unsaturated monomer, although other compositions can be used in the second absorbent layer. Generally, the second absorbent layer functions as a "barrier" between the first absorbent layer (which may partially "disintegrate" when exudate is unevenly, rapidly absorbed or when it absorbs more than about 500%) and the wound. Preferably the second absorbent layer has adhesive properties (or is a pressure sensitive adhesive) and functions to enhance the overall integrity of the wound dressing. In this regard, the second absorbent layer ties the first absorbent layer to a wound-facing layer (or to the wound itself). By having adhesive properties, this second absorbent layer not only aids in controlling the absorption of exudate, but also physically joins other components of the dressing.

As stated above, the first absorbent layer is typically significantly more absorbent than the second absorbent layer, and preferably has an absorbency at least 100 percent greater than the absorbency of the second absorbent layer. The first absorbent layer preferably absorbs at least 400 percent of its weight after immersion in an isotonic saline solution after 24 hours at room temperature.

A typical wound dressing of the present invention preferably includes a porous or non-porous facing layer to provide a fluid permeable barrier between the wound site and the gel layer. The facing layer allows transport of moisture (i.e. fluid and vapor) from the wound to the gel layer and may isolate the wound from other components of the dressing. The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. A preferred facing layer comprises a polyurethane film.

In one useful embodiment, the facing layer is conformable to animal (including human) anatomical surfaces, has a moisture vapor transmission rate (MVTR) of at least 300 grams per square meter per 24 hours at 80% relative humidity differential at 40° C. (per method of Chen, U.S. Pat. No. 5,733,570), is impermeable to liquid water throughout substantially its entire imperforate area and contains perforations means for passing wound exudate through the facing layer. This means that the facing layer does not pass liquid water under normal wound treatment conditions except at the places in the facing layer that are positively perforated to allow the exudate to pass into the reservoir.

The preferred moisture vapor transmission rate of the facing layer is at least 600 grams per square meter per 24 hours at an 80% relative humidity differential at 40° C. The facing layer may further comprise a pressure sensitive adhesive layer. The adhesive coated facing layer preferably has the aforesaid MVTR. Therefore, if the facing layer is impermeable to liquid water except for the perforation means, the adhesive can be permeable to liquid water and vice versa. Porous or non-porous facing layers such as perforated polyamide, polyester, polypropylene, polyethylene, polyetheramide, polyurethanes, chlorinated polyethylene, styrene/butadiene block copolymers (KRATON brand thermoplastic rubber, Shell Chemical Company, Houston, Tex.) and poly(vinyl chloride) and those described in U.S. Pat. No. 3,121,021 (Copeland) that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforation means in the facing layer are holes or slits or other perforations that conduct the passage of liquid water or wound exudate from the wound into the absorbent layer of the wound dressing. The perforations may additionally extend through an adhesive layer, if the front surface of the facing film (that surface facing toward the wound) is coated with a pressure sensitive adhesive layer.

A backing layer may be present in all of the embodiments of the present invention. Preferably the backing layer is conformable to animal anatomical surfaces, impermeable to liquid water and has a moisture vapor transmission rate of at least 600 grams per square meter per 24 hours at an 80% relative humidity differential at 40° C. The backing layer, in combination with a facing layer, may be constructed to form a reservoir (e.g., a pouch or envelope) that surrounds the gel layer, into which the exudate from the wound passes. This reservoir does not permit liquid water or exudate to pass out of it. Instead, the gel layer absorbs the exudate, and moisture in the exudate passes through the backing layer in a vapor form into the atmosphere. The reservoir dressing permits wound exudate to be rapidly removed from the wound site and prevents liquids or bacteria from outside the dressing to contaminate the wound site.

In order to remove moisture vapor, the moisture vapor transmission rate of the backing layer is at least as above noted, and preferably at least 1200 grams per square meter per 24 hours at an 80% relative humidity differential at 40° C.

The preferred embodiments for the facing and backing layers are thin conformable polymeric films. Generally the films are about 12 microns to about 50 microns in thickness, preferably about 12 microns to about 25 microns. Conformability is somewhat dependent on thickness, thus the thinner the film the more conformable the film. Reference has been made herein to the films utilized in the medical article (e.g., wound dressing) of the present invention being conformable to animal anatomical surfaces. This means that when the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful in applicant's invention as facing or backing layers include polyurethanes such as those available under the trade designation ESTANE from B.F. Goodrich, Cleveland, Ohio, elastomeric polyester such as those available under the trade designation HYTREL from E.I. duPont deNemours & Co., Wilmington, Del., blends of polyurethanes and polyesters, polyvinyl chlorides, and polyether-amide block copolymers such as those available under the trade designation PEBAX available from Elf-Atochem. Particularly preferred films for use in the present invention are polyurethane and elastomeric polyester films. The polyurethane and elastomeric polyester films exhibit a resilient property that allows the films to have good conformability. Particularly useful films include "spyrosorbent" films having a differential moisture vapor transmission rate (MVTR). Dressings incorporating spyrosorbent films not only manage wound exudate by absorption, but have the ability to adjust the moisture vapor transmission properties in response to the amount of exudate. Such spyrosorbent films are hydrophilic, moisture vapor permeable and have a relatively high MVTR (wet), and have a differential MVTR ratio (wet to dry) that is greater than 1, and preferably greater than 3:1. The dry MVTR is greater than about 2600 $g/m^2/24$ hrs, preferably about 3000 to 4000 $g/m^2/24$ hrs. A particularly preferred spyrosorbent film, useful as a backing layer, is a segmented polyurethane such as a segmented polyether polyurethane urea based on polytetramethylene glycol and polyethylene glycol polyols. Such a spyrosorbent films are described in U.S. Pat. Nos. 5,653,699 and 4,849,458 (Reed et al.).

Another suitable backing layer is a fluid control film having at least one microstructures-bearing surface with channels that permit directional control of a liquid. This film can be used to transport a fluid to a remote site and thereby facilitate wicking away of a fluid (e.g., wound exudate). Such a film is disclosed in International Publication No. WO 00/42958.

Many different constructions of a wound dressing are possible with the facing layer, the gel layer, and the backing layer. In one embodiment, the areas of the facing layer and the backing layer are greater than that of the gel layer and the facing layer is bonded to the backing layer, thereby forming a pouch, with the gel disposed between the two. In another embodiment, one of the facing or backing layers may be substantially the same area as the gel layer, and the other of greater area. The greater area of the facing or backing layer forms a periphery to which an adhesive layer and a release liner may be attached. It will further be understood that the facing and/or backing layer may be attached or bonded to the adjacent surface of the gel layer to form a contiguous layer construction, in which the backing and facing layers may be the same or of greater area than the gel layer. Alternatively, the backing and facing layers may be bonded to each other, and may or may not be bonded to the gel layer. In these last constructions, the gel layer is constrained within a pouch created by the attachment of the facing and backing layers to each other. The layers may be bonded to each other by any conventional means such as adhesives, heat sealing, or other bonding means.

It is preferred that the facing and backing layers of the medical articles of the present invention be at least translucent and more preferably sufficiently transparent so that the wound site to which they are applied can be viewed through the medical article. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed. It is preferred that the dressing be both transparent and colorless so that the color of the wound, exudate, and periwound skin may also be evaluated. Preferred transparent films for use as facing and backing layers that allow visual inspection of the wound site include polyurethane films such as those available under the trade designation ESTANE from B.F. Goodrich, Cleveland, Ohio; elastomeric polyesters such as those available under the trade designation HYTREL from E.I. duPont deNemours & Co., Wilmington, Del.; and, polyether block amides such as those available under the trade designation PEBAX from Elf Altochem North America, Philadelphia, Pa. Other useful films are those described in U.S. Pat. No. 4,499,896 (Heinecke); U.S. Pat. No. 4,598,004 (Heinecke); and U.S. Pat. No. 5,849,325 (Heinecke et al).

While the facing layer can be attached to the wound by means other than a pressure sensitive adhesive on its surface, it is preferred to use such an adhesive. The presence of the adhesive of the facing layer normally reduces the moisture vapor permeability of the facing layer. Therefore it is preferred that the facing layer is adhesive coated prior to adding a plurality of perforations to the layer. The wound exudate therefore can readily pass through a perforated adhesive coated facing layer. Preferably, both the facing and backing layers are precoated with an adhesive layer to both facilitate bonding of the backing layer to the facing layer (forming a pouch), and bonding of the facing film to the wound site.

The facing layer is normally attached to the wound site by means of adhesive which can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% isooctyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration -A-B-A- wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/N-vinyl pyrrolidone copolymer adhesives and crosslinked acrylate adhesives such as for example those described in U.S. Pat. No. 4,112,213 (Waldman). Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310 (Delgado et al.); a fibrous adhesive with low trauma properties as described in U.S. Pat. No. 6,171,985 B1 (Joseph et al.); or have especially good adhesion to wet skin, such as the adhesives described in U.S. Pat. No. 6,198,016 B1 (Lucast et al.), and International Publication Nos. WO 99/13866 and WO 99/13865; multilayered adhesives as disclosed in U.S. Pat. Publication No. 2001/0051178 A1 (Blatchford et al.). A particularly preferred adhesive includes 15 wt-% acrylic acid, 15 wt-% methoxypolyethylene oxide 400 acrylate, 70 wt-% isooctyl acrylate, prepared according to Example 1 of U.S. Pat. No. 5,849,325 (Heinecke et al.).

The adhesive may be chosen to be permeable to water or wound exudate, or the adhesive may be pattern coated on the front surface of the wound dressing (i.e. the surface in contact with the wound site, whether it is the front surface of the facing or backing layers) so as to not impede the flow of exudate to the gel layer, i.e. the adhesive may be coated at the periphery of the wound dressing. Alternatively the adhesive layer may be perforated as described for the facing film to provide a fluid path for the exudate. A release liner may be attached to the adhesive layer for ease of handling. Examples of release liners are liners made of or coated with polyethylene, polypropylene and fluorocarbons and silicone coated release papers or polyester films. Examples of the silicone coated release papers are POLYSLIK S-8004, 83 pound (135.4 g/m$^2$) bleached silicone release paper supplied by H.P. Smith Co., Chicago, IL, and 80 pound (130.5 g/m$^2$) bleached two-sided silicone coated paper (2-80-BKG-157) supplied by Daubert Chemical Co., Dixon, IL.

A wound dressing of the present invention may also include a frame that allows the dressing to be more easily applied to the wound. The frames are made of a relatively rigid material that maintains the shape of the dressing during handling and application to the wound site. The frame is generally releasably adhered to the back surface of the backing film and is removed after application of the wound dressing. Suitable frames are described in U.S. Pat. No. 5,531,855 (Heinecke et al.) and U.S. Pat. No. 5,738,642 (Heinecke et al.).

An optional patterned surface may be imparted to the gel material by conventional molding techniques. Alternatively, a desired pattern may be imparted using an embossing technique. Examples of such techniques are described in International Publication No. WO 01/60296 A1.

EXAMPLES

The following examples are offered to aid in understanding of the present invention and are not to be construed as limiting the scope thereof. Unless otherwise indicated, all parts and percentages are by weight.

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

Table of Abbreviations

| Abbreviation or Trade Designation | Description |
|---|---|
| JEFFAMINE XTJ-506 | Amine terminal PEO/PPO, commercially available from Huntsman Corp, Houston, TX |
| JEFFAMINE M-2070 | Amine terminal PEO/PPO, commercially available from Huntsman Corp, Houston, TX |
| PEO | Polyethylene oxide |
| PPO | Polypropylene oxide |

-continued

Table of Abbreviations

| Abbreviation or Trade Designation | Description |
|---|---|
| PEO/PPO-silane | Prepared as described in the Preparative Examples section. |
| PEG-methacrylate-silane | Prepared as described in the Preparative Examples section. |
| NALCO 2326 | Nanosilica particle sol with 16% by weight particles of 5 nanometers average particle size commercially available from Nalco Chemical, Naperville, IL. |
| NALCO 2327 | Nanosilica particle sol with 40% by weight particles of 20 nanometers average particle size commercially available from Nalco Chemical, Naperville, IL. |
| SILQUEST A-174 | Methacryloxypropyl trimethoxysilane commercially available from OSi Specialties, Inc., Danbury, CT. |
| M-PEG 400 A | Methoxypolyethylene glycol 400 acrylate from Osaka Organic Chemical Industry, Ltd., Osaka, Japan |
| M-PEG 454 A | Methoxypolyethylene glycol 454 acrylate available from Sigma-Aldrich, Milwaukee, WI. |
| M-PEG MA 300 | Methoxypolyethylene glycol 300 methacrylate available from Sigma-Aldrich, Milwaukee, WI. |
| HEMA | Hydroxyethyl methacrylate |
| MAA-PEG | Methacrylated polyalkylene oxide prepared according to U.S. Pat. No. 7,005,143, Preparative Example 1. |
| IRGACURE 2959 | Photocatalyst commercially available from Ciba Specialty Chemicals, Tarrytown, NY. |
| IRGACURE 819 | Photocatalyst commercially available from Ciba Specialty Chemicals, Tarrytown, NY. |
| PET film | Poly(ethylene terephthalate) release liner film with a thickness of 40 micrometers. |

Test Methods
Absorbency

The absorbency of each exemplary composition was determined by weighing a 2×2 centimeter square of the cured composition, with a thickness of approximately 1.1 millimeters and recording this as "dry weight". The sample was then immersed in approximately 200 milliliters of 0.9 weight percent aqueous NaCl for 24 hours, removed from the solution and the excess liquid was allowed to drip off of the sample for 1 minute. The sample was again weighed and this weight was recorded as "wet weight". The absorbency of each sample was calculated as the increase in sample weight, expressed as a percentage of the dry weight, according to the formula:

$$[(\text{wet weight}-\text{dry weight})/\text{dry weight}]*100=\text{absorbency}$$

Thermogravimetric Analysis

The Thermogravimetric Analysis (TGA) was performed using a TA Instruments TGA 2950 and heating the sample to 550° C. at a rate of 10° C./minute under a nitrogen purge in an aluminum pan. The wt % silica was then determined based on the residual mass after heating.

Compression Testing

Compression testing was done on the swollen films using a TA instruments DMA Q800. The films were immersed in approximately 200 milliliters of 0.9 weight percent aqueous NaCl for 24 hours, removed from the solution and tested immediately. The samples tested were 8 millimeters in diameter and approximately 1 millimeter thick. Samples C5 and 21-23 were three millimeters thick. The samples were strained at a rate of 5% per minute until failure. All of the samples that did not fail were stopped when the load limit of the instrument was reached. The secant modulus was determined at 0.08 MPa by dividing this stress by the corresponding strain for the sample.

Preparative Example 1

Preparation of PEO/PPO-Silane 1

In a glass reaction vessel JEFFAMINE XTJ-506, (50.32 grams) was heated to 40° C. and 3-isocyanatopropyl triethoxysilane (10.33 grams) was added. After shaking for 10 minutes, a yellow solution was formed that slowly crystallized into a waxy solid of the PEO/PPO-silane.

Preparative Example 2

Preparation of PEO/PPO-Silane 2

In a glass reaction vessel JEFFAMINE M-2070, (100.00 grams) and 3-isocyanatopropyl triethoxysilane (12.37 grams) was added. After shaking for 30 minutes, a yellow solution of the PEO/PPO-silane 2 was formed.

Preparative Example 3

Preparation of PEG-Methacrylate-Silane

In a glass reaction vessel poly(ethylene glycol (400) monomethacrylate (Polysciences) (50.00 grams), 3-isocyanatopropyl trimethoxysilane (19.51 grams), triethylamine (9.60 grams) and butylated hydroxytoluene (0.01 grams) were added. The contents were heated at 45° C. for three hours. Residual triethylamine was removed under vacuum to yield the product.

Example 1

To Nalco 2326 (100.00 grams) a solution of PEO/PPO-silane 1 (21.6 grams, 0.018 moles), SILQUEST A-174 (4.48 grams, 0.018 moles) and 1-methoxy-2-propanol (150 grams) was added slowly over 15 minutes. The mixture was heated to 80° C. with mechanical stirring for 24 hours. After cooling, M-PEG 400 A (30.00 grams) was added and the mixture was placed under vacuum to remove solvents. A clear, transparent solution was obtained (68.91 grams).

Example 2

To Nalco 2326 (150.00 grams) a solution of SILQUEST A-174 (13.43 grams, 0.054 moles) and 1-methoxy-2-propanol (175 grams) was added slowly over 15 minutes. The mixture was heated to 80° C. with mechanical stirring for 24 hours. After cooling, HEMA (34.6 grams) was added and the mixture was placed under vacuum to remove solvents. A clear, transparent solution was obtained (87.5 grams).

Example 3

To Nalco 2327 (100.00 grams) a solution of PEO/PPO-silane 2 (30.00 grams, 0.015 moles), SILQUEST A-174 (2.46 grams, 0.010 moles) and 1-methoxy-2-propanol (150 grams) was added slowly over 15 minutes. The mixture was heated to 80° C. with mechanical stirring for 24 hours. After cooling, M-PEG 300 MA (80.0 grams) was added and the mixture was placed under vacuum to remove solvents. A clear, transparent solution was obtained (154.2 grams).

Example 4

To Nalco 2327 (50.00 grams) a solution of PEO/PPO-silane 2 (15.00 grams, 0.007 moles), SILQUEST A-174 (1.23 grams, 0.005 moles) and 1-methoxy-2-propanol (75 grams) was added slowly over 15 minutes. The mixture was heated to 80° C. with mechanical stirring for 24 hours. After cooling, M-PEG A 400 (40.0 grams) was added and the mixture was placed under vacuum to remove solvents. A clear, transparent solution was obtained (79.1 grams).

Example 5

To Nalco 2326 (50.00 grams) a solution of PEG-methacrylate-silane (14.33 grams, 0.007 moles) and 1-methoxy-2-propanol (75 grams) was added slowly over 10 minutes. The mixture was heated to 95° C. with mechanical stirring for 24 hours. After cooling, 30 grams of the above solution and M-PEG A 400 (7.5 grams) were mixed and the mixture was placed under vacuum to remove all solvents. A clear, transparent solution was obtained Examples 6-22 and Comparative Examples C1-C5

For Examples 6-23 and Comparative Example C1-C4, a series of films were prepared by mixing the components listed in Table 1 in a vial. The mixtures were purged with nitrogen for 10 minutes and then poured into a square TEFLON mold (39×39×1.5 millimeters). A layer of PET film was then placed on top of the film. This construction was irradiated for 30 minutes using a Sylvania F40/350 BL lamp (available from OSRAM SYLVANIA, Danvers, Mass.) with the sample approximately 2.5 centimeters from the lamp. The absorbency of each exemplary composition was determined by using the Absorbency test method listed above. The Absorbency test and the data are listed in Table 8. Additionally samples were tested according to the TGA Analysis and Compression Testing test methods listed above, the data are listed in Table 8.

TABLE 1

| Example | Weight of Particle sample with M-PEG 400 A from Example 1 (grams) | M-PEG 400 A (grams) | HEMA (grams) | IRGACURE 2959 (g) | IRGACURE 819 (g) |
| --- | --- | --- | --- | --- | --- |
| C1 | 0 | 6.50 | 3.50 | 0.050 | 0.050 |
| 6 | 1.00 | 5.93 | 3.07 | 0.050 | 0.050 |
| 7 | 2.00 | 5.36 | 2.64 | 0.050 | 0.050 |
| 8 | 3.00 | 4.79 | 2.21 | 0.050 | 0.050 |
| 9 | 4.00 | 4.22 | 1.78 | 0.050 | 0.050 |

TABLE 2

| Example | Weight of Particle sample with HEMA from Example 2 (grams) | M-PEG 454 A (grams) | HEMA (grams) | IRGACURE 2959 (g) | IRGACURE 819 (g) |
| --- | --- | --- | --- | --- | --- |
| C2 | 0 | 6.50 | 3.50 | 0.050 | 0.050 |
| 10 | 1.00 | 5.85 | 2.60 | 0.050 | 0.050 |
| 11 | 3.00 | 3.90 | 0.45 | 0.050 | 0.050 |

TABLE 3

| Example | Weight of Particle sample with HEMA from Example 2 (grams) | MAA-PEG (grams) | M-PEG 454 A (grams) | HEMA (grams) | IRGACURE 2959 (g) | IRGACURE 819 (g) |
|---|---|---|---|---|---|---|
| C3 | 0 | 2.00 | 6.00 | 2.00 | 0.050 | 0.050 |
| 12 | 1.00 | 1.91 | 5.73 | 1.36 | 0.050 | 0.050 |
| 13 | 3.00 | 1.73 | 5.19 | 0.43 | 0.050 | 0.050 |

TABLE 4

| Example | Weight of Particle sample with M-PEG 400 A from Example 1 (grams) | MAA-PEG (grams) | M-PEG 454 A (grams) | HEMA (grams) | IRGACURE 2959 (g) | IRGACURE 819 (g) |
|---|---|---|---|---|---|---|
| C4 | 0 | 2.00 | 6.50 | 1.50 | 0.050 | 0.050 |
| 14 | 1.00 | 1.90 | 5.68 | 1.43 | 0.050 | 0.050 |
| 15 | 3.00 | 1.70 | 4.03 | 1.28 | 0.050 | 0.050 |

TABLE 5

| Example | Weight of Particle sample with M-PEG 300 MA from Example 3 (grams) | MAA-PEG (grams) | M-PEG 454 A (grams) | HEMA (grams) | IRGACURE 2959 (g) | IRGACURE 819 (g) |
|---|---|---|---|---|---|---|
| 16 | 1.00 | 1.91 | 5.66 | 1.44 | 0.050 | 0.050 |
| 17 | 3.00 | 1.73 | 3.98 | 1.30 | 0.050 | 0.050 |

TABLE 6

| Example | Weight of Particle sample with M-PEG 400 A from Example 4 (grams) | MAA-PEG (grams) | M-PEG 454 A (grams) | HEMA (grams) | IRGACURE 2959 (g) | IRGACURE 819 (g) |
|---|---|---|---|---|---|---|
| 18 | 1.00 | 1.90 | 5.68 | 1.43 | 0.050 | 0.050 |
| 19 | 3.00 | 1.70 | 4.03 | 1.28 | 0.050 | 0.050 |

TABLE 7

| Example | Weight of Particle sample with M-PEG 400 A from Example 5 (grams) | M-PEG 454 A (grams) | HEMA (grams) | IRGACURE 2959 (g) | IRGACURE 819 (g) |
|---|---|---|---|---|---|
| C5 | 0 | 5.6 | 2.7 | 0.04 | 0.04 |
| 20 | 1.00 | 5.00 | 2.70 | 0.04 | 0.04 |
| 21 | 2.00 | 3.00 | 1.62 | 0.03 | 0.03 |
| 22 | 3.00 | 2.50 | 1.35 | 0.03 | 0.03 |

TABLE 8

| Example | Absorbency | Weight % Silica by TGA Test | Compression Test Stress at failure (MPa) | Secant Modulus at 0.08 MPa (Pa) |
|---|---|---|---|---|
| C1 | 691 | 0 | 0.12 | $1.09 \times 10^5$ |
| 6 | 505 | 3.3 | Did not fail | $1.46 \times 10^5$ |
| 7 | 379 | 5.5 | Did not fail | $2.17 \times 10^5$ |
| 8 | 273 | 8.9 | Did not fail | $3.32 \times 10^5$ |
| 9 | 207 | 11.2 | Did not fail | $5.60 \times 10^5$ |
| C2 | 515 | 0 | 0.13 | $1.44 \times 10^5$ |
| 10 | 379 | 2.9 | Did not fail | $1.78 \times 10^5$ |
| 11 | 115 | 11.9 | Did not fail | $5.10 \times 10^5$ |
| C3 | 478 | 0 | Did not fail | $1.92 \times 10^5$ |
| 12 | 387 | 2.2 | Did not fail | $2.63 \times 10^5$ |
| 13 | 194 | 7.6 | Did not fail | $5.72 \times 10^5$ |
| C4 | 532 | 0 | Did not fail | $1.66 \times 10^5$ |
| 14 | 433 | 2.5 | Did not fail | $2.28 \times 10^5$ |
| 15 | 254 | 6.9 | Did not fail | $3.98 \times 10^5$ |
| 16 | 467 | 2.3 | Did not fail | $1.75 \times 10^5$ |
| 17 | 345 | 6.9 | Did not fail | $2.66 \times 10^5$ |
| 18 | 479 | 1.8 | Did not fail | $1.95 \times 10^5$ |
| 19 | 428 | 5.6 | Did not fail | $2.00 \times 10^5$ |
| C5 | 471 | 0 | 0.07 | 0.08 MPa stress not achieved |
| 21 | 456 | 1.8 | 0.13 | $1.95 \times 10^5$ |

TABLE 8-continued

| Example | Absorbency | Weight % Silica by TGA Test | Compression Test Stress at failure (MPa) | Secant Modulus at 0.08 MPa (Pa) |
|---|---|---|---|---|
| 22 | 267 | 5.1 | Did not fail | $4.43 \times 10^5$ |
| 23 | 198 | 7.6 | Did not fail | $6.50 \times 10^5$ |

What is claimed is:

1. A cured composition comprising the reaction product of:
   a) 1 to 20 parts by weight of a surface modified nanoparticle component having ethylenically unsaturated groups and hydrophilic poly(alkylene oxide) groups, wherein the average particle size of said nanoparticle component, prior to surface modification, is 20 nanometers or less; and
   b) 80 to 99 parts by weight of a monomer component comprising:
   a monofunctional poly(alkylene oxide) free-radically polymerizable macromonomer having a poly(alkylene oxide) moiety, and wherein the parts by weight of a) and b) are based on 100 parts by weight of the total cured composition.

2. The cured composition of claim 1 wherein the monofunctional poly(alkylene oxide) free-radically polymerizable macromonomer is of the formula:

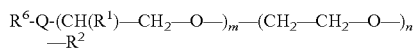

wherein $R^6$ is a an ethylenically unsaturated polymerizable group;
$R^1$ is a $(C_1\text{-}C_4)$ alkyl group,
$R^2$ is H or $R^1$,
Q is —O—, —S— or —NR$^2$—,
n is at least 5, m may be 0, n+m is at least 5, and the mole ratio of n:m is at least 2:1.

3. The cured composition of claim 2, wherein m is at least 1 and the mole ratio of n to m (n:m) is greater than 2:1.

4. The cured composition of claim 2 where $R^6$ is selected from the group consisting of:

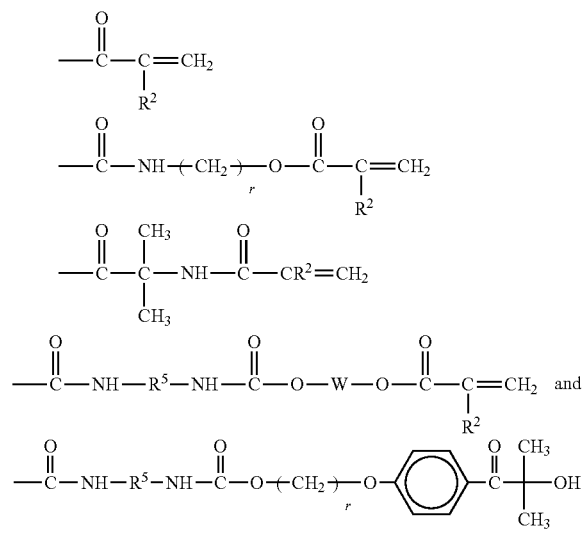

wherein
$R^2$ is H or $R^1$,
$R^1$ is a $C_1$ to $C_4$ alkyl,
$R^5$ is an aromatic group, aliphatic group, alicyclic group, or combinations thereof, W is an alkylene or poly(alkylene oxide) group, and r=2-10.

5. The cured composition of claim 1 wherein the surface modified nanoparticles comprise inorganic nanoparticles modified by a first surface modifying agent having an ethylenically unsaturated group and a second surface modifying agent having poly(alkylene oxide) groups.

6. The cured composition of claim 1 wherein the nanoparticles are selected from the group consisting of silica, alumina, tin oxide, iron oxide, zirconia, vanadia, titania; and combinations thereof.

7. The cured composition of claim 1 wherein the average particle size of said nanoparticle component, prior to surface modification, is less than 10 nanometers.

8. The cured composition of claim 5 wherein said first surface modifying agent is of the formula Y—R$^3$—Si—(OR$^4$)$_b$(R$^4$)$_{3-b}$, wherein:
   $R^3$ is a covalent bond or a polyvalent hydrocarbon bridging group, Y is an ethylenically unsaturated polymerizable group,
   $R^4$ is independently an alkyl, aryl, or aralkyl group of 1 to 8 carbon atoms optionally substituted in available positions by oxygen, nitrogen and/or sulfur atoms; and b is 1 to 3.

9. The cured composition of claim 5 wherein said second surface modifying agent is of the formula R$^2$—(OCH$_2$CH$_2$—)$_n$(OCH$_2$CH(R$^1$))$_m$-Q'-R$^3$—Si—(OR$^4$)$_b$(R$^4$)$_{3-b}$, wherein
   Q' is a divalent linking group;
   $R^1$ is a $C_1$ to $C_4$ alkyl group,
   $R^2$ is $R^1$ or H,
   $R^3$ is a covalent bond or a divalent hydrocarbon bridging group;
   $R^4$ is independently an alkyl, aryl, or aralkyl group of 1 to 8 carbon atoms optionally substituted by catenary oxygen, nitrogen and/or sulfur atoms;
   n is at least 5, m may be 0, and the mole ratio of n:m is at least 2:1; and
   b is 1 to 3.

10. The cured composition of claim 5 wherein the ratio of hydrophilic poly(alkylene oxide) groups to ethylenically unsaturated groups on the surface of the inorganic nanoparticles is 1:10 to 10:1.

11. The cured composition of claim 5 wherein said first surface modifying agent is used in amounts sufficient to react with at least 10%, preferably 10% to 90% of the available functional groups on the surface of the inorganic nanoparticles.

12. The cured composition of claim 1 wherein the monomer component comprises:
   a) 30 to 80 wt. % of a monofunctional poly(alkylene oxide) free-radically polymerizable macromonomer having a poly(alkylene oxide) moiety;
   b) 5 to 40 wt. % of a polar monomer;
   c) 0 to 20 wt. % of a hydrophobic monomer;
   d) 0 to 20 wt. % of a multifunctional poly(alkylene oxide) free-radically polymerizable macromonomer having a poly(alkylene oxide) moiety, based on 100 wt. % of the total cured composition.

13. The cured composition of claim 12 comprising 0.1 to 20 wt. % of said multifunctional poly(alkylene oxide) free-radically polymerizable macromonomer, based on 100 wt. % of the total cured composition.

14. The cured composition of claim 8, wherein $R^3$ is a poly(alkylene oxide) group.

* * * * *